(12) United States Patent
Liu et al.

(10) Patent No.: US 8,485,974 B2
(45) Date of Patent: Jul. 16, 2013

(54) MULTIPLE-FREQUENCY ULTRASONIC PHASED ARRAY DRIVING SYSTEM

(75) Inventors: Hao-Li Liu, Taoyuan County (TW); Hsu Chang, Fremont, CA (US); Sheng-Fu Chen, Zhunan Town (TW)

(73) Assignee: National Health Research Institutes, Miaoli County (TW)

( * ) Notice: Subject to any disclaimer, the term of this patent is extended or adjusted under 35 U.S.C. 154(b) by 288 days.

(21) Appl. No.: 12/946,256

(22) Filed: Nov. 15, 2010

(65) Prior Publication Data

US 2012/0123302 A1    May 17, 2012

(51) Int. Cl.
*A61B 8/00*    (2006.01)

(52) U.S. Cl.
USPC ........... 600/437; 600/441; 600/407; 600/443; 600/447

(58) Field of Classification Search
USPC .......................... 600/407, 437, 441, 443, 447
See application file for complete search history.

(56) References Cited

U.S. PATENT DOCUMENTS

| | | | |
|---|---|---|---|
| 5,997,479 A * | 12/1999 | Savord et al. ............. | 600/447 |
| 6,419,648 B1 | 7/2002 | Vitek et al. | |
| 8,282,581 B2 * | 10/2012 | Zhao et al. ............. | 601/2 |
| 2003/0055337 A1 | 3/2003 | Lin | |
| 2008/0051680 A1 | 2/2008 | Luebcke | |
| 2008/0071165 A1 | 3/2008 | Makin et al. | |
| 2008/0228077 A1 | 9/2008 | Wilk et al. | |
| 2009/0149781 A1 | 6/2009 | Liu et al. | |

FOREIGN PATENT DOCUMENTS

| | | |
|---|---|---|
| CN | 1768877 | 5/2006 |
| JP | 2009/183147 | 8/2009 |
| TW | 422711 | 5/2000 |

OTHER PUBLICATIONS

Ji et al., High-intensity focused ultrasound with large scale spherical phased array for the ablation of deep tumors, *Journal of Zhejiang University Science B, 10(9): 639-647.*

* cited by examiner

*Primary Examiner* — Unsu Jung
*Assistant Examiner* — Joel Lamprecht
(74) *Attorney, Agent, or Firm* — Occhiuti Rohlicek & Tsao LLP (57) ABSTRACT

An apparatus for sonicating a patient includes an ultrasound array having a plurality of transducers; a driving module for driving said transducers; and a control kernel for causing said driving module to drive said transducers concurrently at two different frequencies.

11 Claims, 10 Drawing Sheets

MULTIPLE-FREQUENCY ULTRASONIC PHASED ARRAY DRIVING SYSTEM

FIELD OF DISCLOSURE

This disclosure relates to ultrasonic imaging systems, and in particular, to drivers for ultrasonic arrays.

BACKGROUND

Ultrasound has been shown to have a number of clinical applications. Among these are thermal therapy, enhancement of sono-chemical reactions, and vibroacoustography.

When used for thermal therapy, ultrasonic energy is directed deep within tissue. As the tissue absorbs energy, its temperature rises by as much as 30-55 degrees C. It does so rapidly enough so that heat has no time to dissipate significantly into surrounding tissue. As a result, the ultrasound can cause necrosis and/or coagulation of the target tissue without inflicting significant harm on surrounding tissue. Because this procedure is non-invasive, no surgery is required, thus reducing the cost of therapy.

Another clinical application of ultrasound is that of enhancing sonochemical reactions for therapeutic purposes. Sonochemical reactions in liquids are known to arise from acoustic cavitation, a process that begins with nucleation, followed by growth and collapse of microscopic bubbles. The high temperatures (several thousand degrees Celsius) and high pressures (several hundred atmospheres) temporarily created in the vicinity of the bubble as it collapses are believed to trigger sonochemical reactions. Such sonochemical reactions are known to be enhanced in the process of multiple sonication frequencies.

Yet another application of clinical ultrasound is ultrasound-stimulated vibro acoustography (USVA) to create a map of the mechanical response of object to a force that is applied at each point on the object. USVA involves simultaneous output of two similar frequencies to cause spatial interference that contains, as one component thereof, a frequency-difference component having a frequency that is much lower than either of the frequencies used for sonication. In response to the force at the this difference frequency, a portion of the object vibrates. The size of this portion, and the pattern of the resulting motion, depend in part on the object's viscoelastic characteristics. The acoustic field resulting from object vibration is then detected by a hydrophone and used to form an image of the object. Because of the high spatial definition of ultrasound radiation force and high motion-detection sensitivity offered by the hydrophone, this method can identify changes in the elasticity of soft tissue, which in turn is useful for diagnosis.

A difficulty that can arise in the use of ultrasound in these and other applications is its propensity to generate standing waves when propagation occurs inside certain cavities. For example, when transcranial ultrasound is used to deliver energy into the brain, a standing wave can arise within the cranium. This standing wave can form local hot spots, or concentrations of energy.

A known way to apply ultrasonic energy in any of the above applications is to use an ultrasound phased arrays having multiple transducers. Unlike a single-element transducer, which has a fixed focus produced at a geometric center thereof, an ultrasound phased array can steer the ultrasonic energy focus to an arbitrary position. This is typically achieved by driving each transducer with a signal of the appropriate phase. Such an array can also achieve dynamic focal beam scanning by electronically altering the relative phases of the transducer signals.

However, known ultrasonic phased arrays are hampered in their ability to enhance any of the above treatment modalities by difficulties associated with simultaneously outputting multiple frequencies.

SUMMARY

In one aspect, the invention features an apparatus for sonicating a patient. Such an apparatus includes an ultrasound array having a plurality of transducers; a driving module for driving the transducers; and a control kernel for causing the driving module to drive the transducers concurrently at two different frequencies.

In some embodiments, the control kernel includes a master microcontrol unit and a plurality of slave microcontrol units, each of the slave microcontrol units being configured to control a subset of the transducers. In such embodiments, the master microcontrol unit provides instructions to the slave microcontrol units. Among these embodiments are those that also include a plurality of floating point gate arrays, and wherein each of the slave microcontrol units is in data communication with a subset of the gate arrays, those that also include a dual stage VCO/PLL circuit, and those that include a plurality of multiplexers, each of which receives waveforms having different frequency, and wherein each of the slave microcontrollers is configured to select, from each of a subset of the multiplexers, a waveform having a particular frequency.

Among the embodiments that feature a dual stage VCO/PLL circuit are those in which the dual stage VCO/PLL circuit includes a first stage that receives a waveform having a first particular frequency and scales that first particular frequency by a first scale factor, and a second stage that receives a waveform having a second particular frequency and scales that second particular frequency by a second scale factor.

In other embodiments, the apparatus also includes a power sensing circuit for providing, to the control kernel, information concerning an extent to which power is output by the transducers.

Yet other embodiments feature a control kernel further configured to drive at least one of the transducers at least two frequencies simultaneously.

In another aspect, the invention features an apparatus for sonicating a patient. Such an apparatus includes an ultrasound array having a plurality of transducers; a driving module for driving the transducers; and means for causing the driving module to drive the transducers concurrently at two different frequencies.

In another aspect, the invention features a method for sonicating a target. Such a method includes directing an ultrasound array having a plurality of transducers toward the target; selecting a plurality of frequencies; and causing the array to concurrently illuminate the target using each of the frequencies.

Specific practices of the invention include those in which causing the array to concurrently illuminate includes causing different transducers to be excited at different frequencies, and those in which causing the array to illuminated includes causing a transducer to be concurrently excited at different frequencies.

Other practices include feedback indicative of an extent to which power is output by the array.

In additional practices, causing the array to concurrently illuminate includes providing a master and a plurality of slaves, each slave being configured to control a subset of transducers, the master being configured to provide instructions to a slave for causing the slave to control the transducers. Among these are practices that also include providing floating point gate arrays, and providing data communication between each slave and a subset of the gate arrays.

These and other features of the invention will be apparent from the following detailed description, and the accompanying figures, in which:

DETAILED DESCRIPTION

Control Kernel

Figure 1:
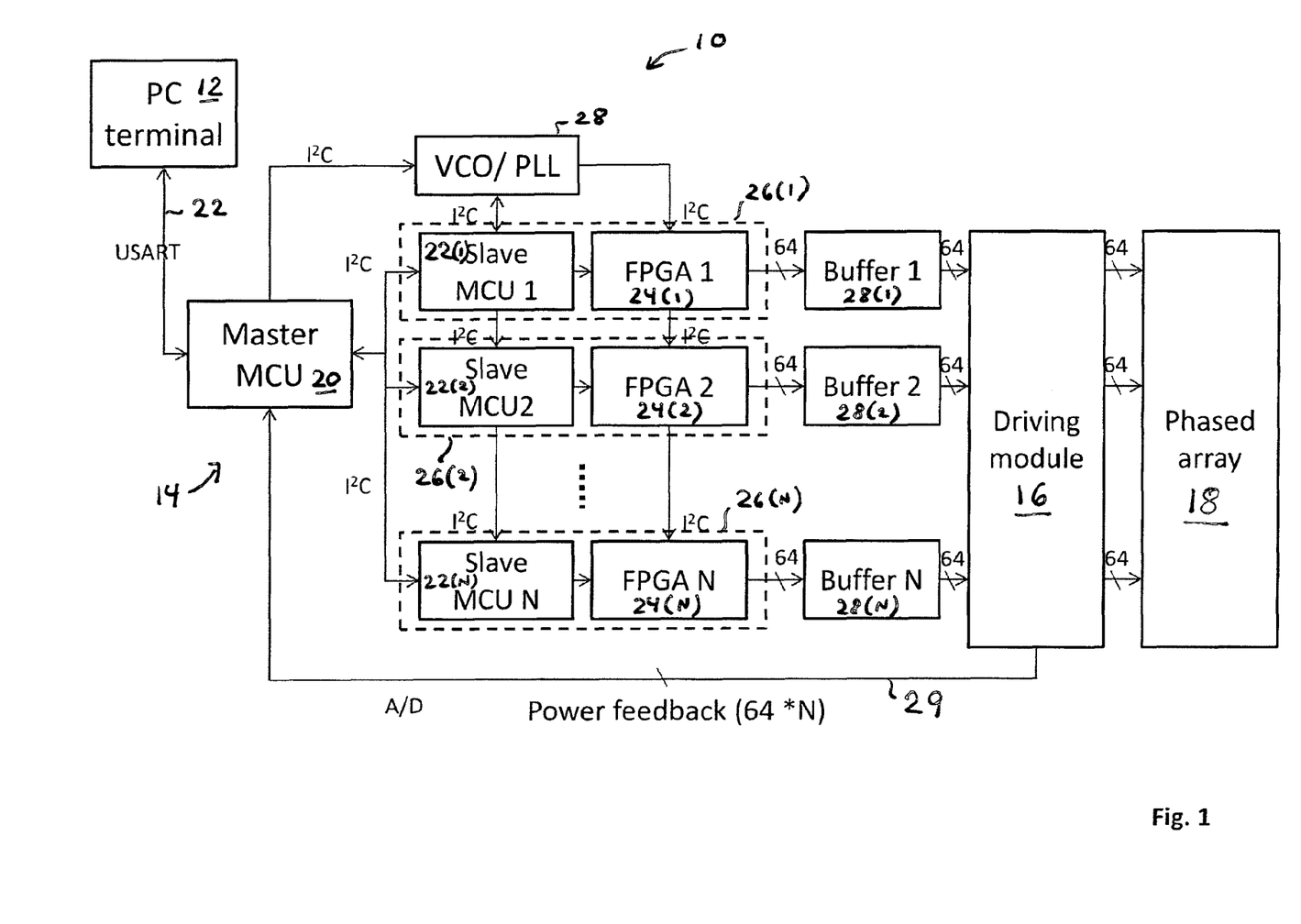
FIG. 1 shows an overall architecture of a multiple-channel ultrasonic driving system.

Referring to FIG. 1, an ultrasound imaging system 10 includes a PC terminal 12 that communicates with a two-stage control kernel 14. The control kernel 14 in turn communicates with a multi-channel driving module 16 for driving ultrasound transducers on an ultrasound phased array 18.

The control kernel 14 includes a master micro control unit (MCU) 20 and slave MCUs 22(1-N). In general, the number of slave MCUs 22(1-N) depends on the number of ultrasound transducers on the ultrasound phased array 18. Each slave MCU 22(1-N) controls a corresponding floating point gate array (FPGA) 24(1-N).

In the embodiment shown in FIG. 1, the master MCU 20 receives, from the PC terminal 12 through a USART (universal asynchronous receiver/transmitter) link 22, designated sonication parameters for each ultrasonic transducer. This sonication parameters, which can be controlled on a per-transducer basis, include the frequency at which the ultrasonic transducer is to operate, its power, burst length, pulse repetition frequency (PRF), and the relative phase differences between transducers. The master MCU 20 further provides power control using a pulse-width-modulation (PWM) output port to alter the DC output voltage of a voltage-controlled buck converter. In one embodiment, the PWM output ranges from 0 to 100% at 8-bit resolution. A suitable master MCU 20 is the commercially available 8-bit unit PIC18F452, which is available from Microchip Corp. in Chandler, Ariz., USA.

As shown in FIG. 1, each slave-MCU 22(1-N) operates in conjunction with its corresponding FPGA 24(1-N) to form an integrated MCU/FPGA module 26(1-N). Each such integrated MCU/FPGA module 26(1-N) provides a 64-channel signal output 25(1-N). Multiple MCU/FPGA modules 26(1-N) in the control kernel 14 enable the control kernel 14 to provide more than 64 channels of signal output. For example, if four MCU/FPGA modules 26(1-4) are present, there would be a total of 256 channels of output, with 64 being contributed by each one of the four MCU/FPGA modules 26(1-4).

Within a particular MCU/FPGA module 26(1), the slave MCU 22(1) provides, to its associated downstream FPGA 24(1), frequency commands for the channels controlled by the FPGA 24(1) and phase differences among the channels controlled by the FPGA 24(1). The master MCU 20 receives, from a directional coupler within the driving module 16 and through an A/D input port, an analog feedback signal carrying information about the output power being provided by a piezoelectric element associated with each channel, which it then transmits back to the master MCU 20 via an inter-integrated communication (I²C) protocol link 28.

Each FPGA has an I/O terminal used to provide a 64-bit control signal, which contains specified frequency and phase under a synchronized triggered signal, to the downstream driving modules 16(1-N). Between the FPGA's I/O output and the driving modules 16(1-N) are corresponding buffer circuits 28(1-N) to pull-up the current.

Power-sensing circuits in the driving modules 16(1-N) provide feedback signals 29 indicative of transmitted and reflected power. These feedback signals 29 are provided back to the master MCU 20 and uploaded to the PC-terminal 12 through the USART communication protocol link 22. As a result, real-time updates of individual power consumption and efficiency for each channel can be shown on the PC terminal monitor 12.

Simultaneous Multiple-Frequency Generation

Each MCU/FPGA module 26(1-N) is configured to simultaneously generate multiple frequencies at each channel output. This is achieved by feeding a high-frequency (e.g. 20 MHz) signal from an oscillating crystal to a phase-locked-loop/voltage controlled oscillator (PLL/VCO) module 28.

The PLL/VCO module 28 achieves its extended frequency range by using a two-stage PLL circuit. A first stage of the PLL/VCO module 28 scales the frequency by a small scale factor, for example, up to 40 MHz, so that a frequency divider can output a frequency in a low frequency range. A second stage of the PLL/VCO module 28 scales the frequency by a larger scale factor, for example, up to 160 MHz) so that a frequency divider can output a frequency in a higher frequency range. A simple calculation of the generated frequency provided at the output of the PLL/VCO module 28 is as follows:

$$F_{VCO} = (S1*S2+A)*F_{OSC}*S_{VCO}/DR$$

where $F_{VCO}$ is the output frequency from the PLL/VCO module 28,

S1 and S2 are scale factors associated with the first and second stages respectively, A is a constant offset, $S_{VCO}$ is the scalar tuned by the VCO, which ranges from 0 to 1 as the voltage provided to the VCO ranges from 0 to 5V, $F_{OSC}$ is the input frequency provided by the oscillating crystal to the PLL/VCO module 28, and DR is a programmable frequency-dividing constant associated with a frequency divider integrated into the FPGA.

Figure 2:
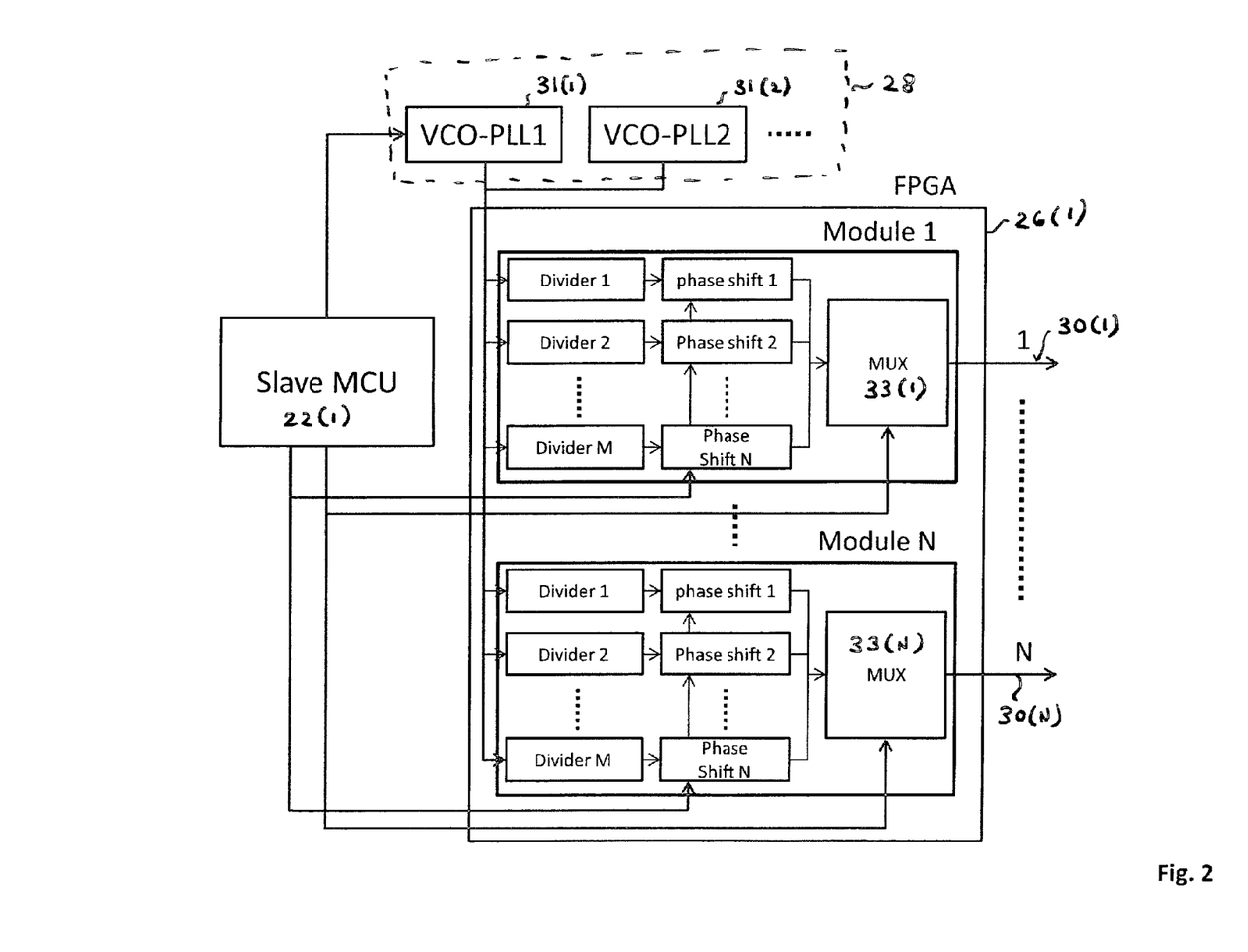
FIG. 2 shows the detailed architecture of one of the slave MCU/FPGA modules from FIG. 1.

Since S1, S2, $S_{VCO}$, and DR can all be controlled by the slave MCU 22(1-N), an arbitrary frequency can be generated and provided to the FPGA 26(1-N). A single PLL/VCO module 28 can thus provide one tunable output frequency to a downstream channel 30(1-N). By having multiple PLL/VCO modules 31(1), 31(2) available in a control kernel 14, as shown in FIG. 2, a slave MCU 22(1-N) can use multiplexers 33(1-N) to select different frequencies for its channel output. For example, a control kernel 14 can designate a first channel group to output a first designated frequency, a second channel group to output a second designated frequency, and so on.

Ideally, M independent PLL/VCO modules 31(1-M) will make M different frequencies available to be directed among the channels. In one embodiment, an output frequency ranging from 0.25 MHz to 4 MHz, with a frequency resolution of 5 kHz can be generated with two embedded PLL/VCO modules. In another embodiment, two frequencies can be provided concurrently, (for example, 1 MHz for a first channel group 1 and 1.5 MHz for a second channel group).

In another embodiment, two or more frequencies are provided to a single channel. The channel in such a case would carry a signal that is a superposition of multiple frequencies. This enables an ultrasonic transducer associated with that channel to be drive simultaneously at two or more frequencies.

Phase Control

In one embodiment, the FPGA 24(1-N) implements a 32-channel phase-assignment unit with 8-bit phase resolution. One advantage of such an FPGA 24(1-N) is that it includes a phase-locked loop module that can be used both for frequency multiplication and to control the phase on multiple channels. A suitable commercially available FPGA is the Cyclone EP1C12, made by Altera Corp, San Jose, Calif., USA.

Figure 3:
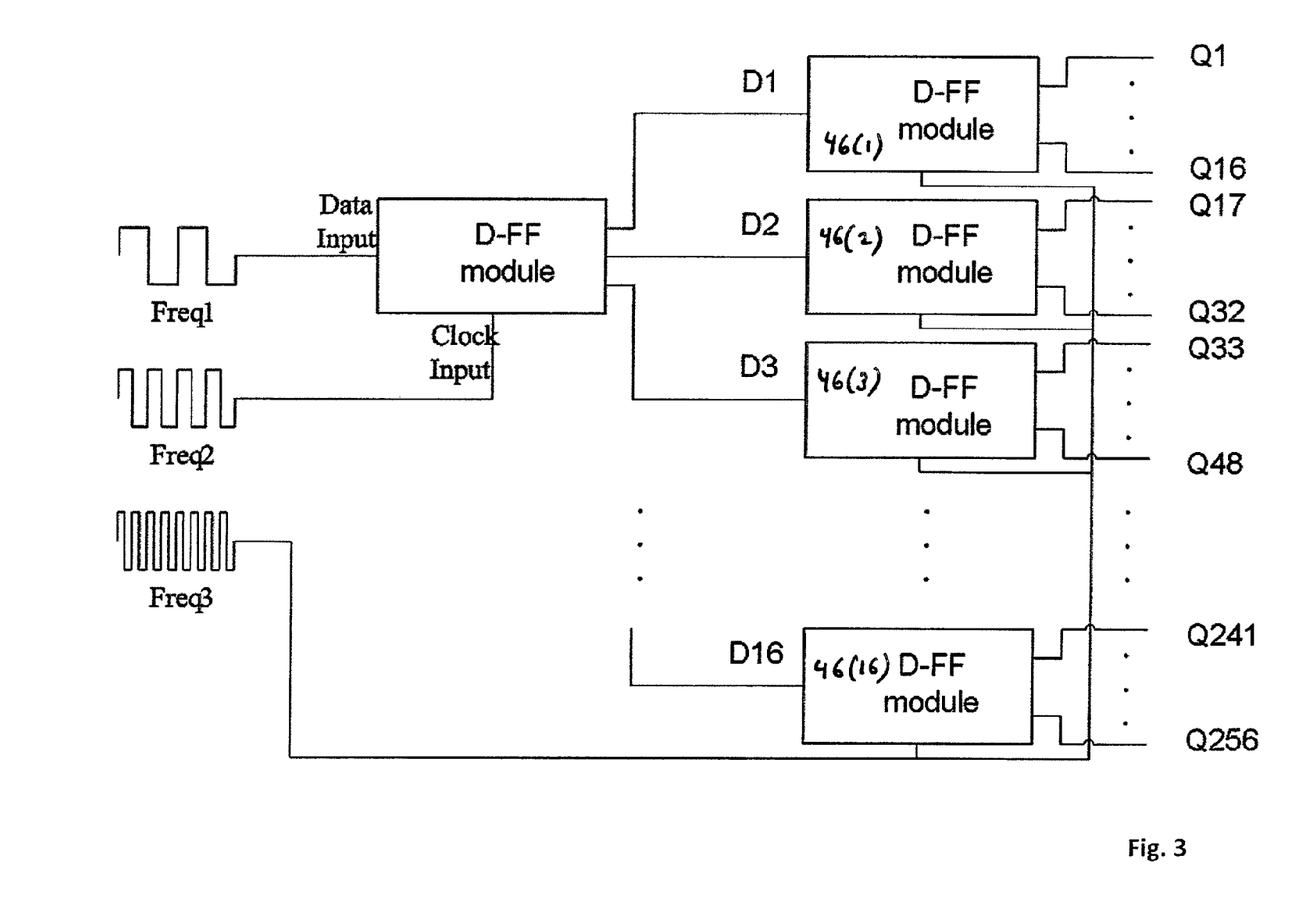
FIG. 3 shows an architecture for achieving 8-bit resolution phase control in the control kernel of FIG. 1, with the upper portion showing a D-flip-flop module design and the lower portion showing a two-stage D-flip-flop module cascaded to generate 8-bit resolution phase control.

A two-stage logic state circuit efficiently uses the logic elements within the FPGA 24(1-N). Referring to FIG. 3, in each stage, 16 D flip-flops (DFF) 46(1-16) are cascaded to provide a 16-step signal delay, with the delay's temporal resolution being determined by an input clock. For the first and second stages of the state machine unit, the clock input frequency is multiplied by a one- or two-stage embedded PLL module with multiplication factors of 16 and 256 (i.e., $16^2$) to provide rough-tuning and fine-tuning of input signal delays, respectively. In the foregoing example, rough tuning would be done with a relatively coarse phase increment of 22.5 degrees, while fine tuning would use a finer phase increment of 1.4 degrees. The foregoing implementation yields $N^2$ possible phase angles with only about 2N logic elements (rather than $N^2$ elements) to perform the 8-bit signal phasing.

For burst mode excitation, a simple latch circuit is implemented in the FPGA 24(1-N). The controllable parameters of the burst-mode single output include burst length, PRF, and the total number of bursts provided from the upstream master MCU.

Driving Module

Figure 4:
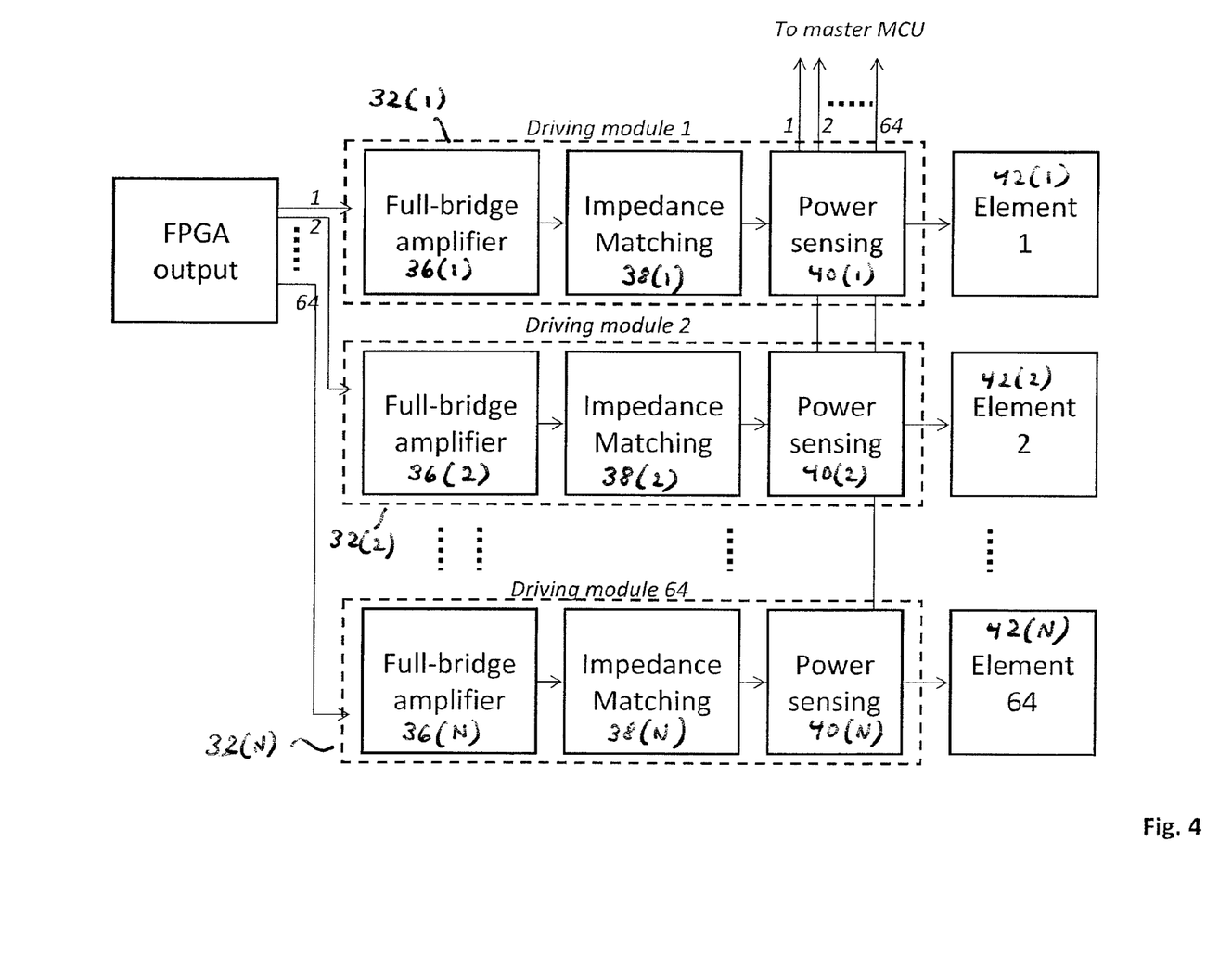
FIG. 4 shows an architecture of a driving module controlled by each MCU/FPGA module in FIG. 1.

Referring now to FIG. 4, the driving module 16 includes driving circuits 32(1-N) for each channel (i.e. N=64 for the embodiment shown). Each driving circuit 32(1-N) includes a PWM controllable power supply and a high-voltage inverter, which in the illustrated embodiment are implemented using a full-bridge amplifier, 36(1-N), an impedance matching circuit 38(1-N), and a power sensing circuit 40(1-64).

The PWM-controllable DC power supply provides an output DC voltage derived from a buck circuit whose output voltage is controlled by a PWM signal from the control kernel 14. The power output for each channel is controlled by altering the voltage in steps defined by an 8-bit resolution. The maximum power output in the illustrated embodiment is 10 watts for each channel. Such an output is sufficient for cavitation-related therapeutic enhancement (for example, for delivery of small therapeutic molecules, DNAs, peptides, etc., into cells or soft tissues), or for direct thermal ablation of tissue within a few seconds.

The high-voltage inverter 36(1-N) transforms the high-voltage square wave into a high-voltage sinusoidal wave. A full-bridge inverter is used to generate a high-voltage square wave, with high-voltage diodes used to cope with the high-voltage switching transients such as overshoots.

The impedance-matching circuit 38(1-N) is useful because the output impedance of the inverter 36(1-N) results in an impedance mismatch of at least two orders of magnitude. Consequently, without impedance matching, power transfer to the transducers 42(1-N) would be inefficient. A typical impedance-matching circuit 38(1-N) is implemented by using two transformer stages with an intermediate LC-resonance stage. Fine tuning the impedance-matching circuit 38(1-N) for each channel allows a high-voltage sinusoidal wave with the required frequency and power to be fed to the ceramic elements.

Finally, a power sensing circuit 40(1-N), which includes a directional coupler, is provided for power monitoring. The power sensing circuit 40(1-N), which is mounted between the transducer and the impedance matching circuit 38(1-N), is designed to monitor the transmitted and reflected power based on the feedback of the two voltages representing the transmitted and reflected power. The voltage standing-wave ratio (SWR), which is regarded as a measure of the power transfer efficiency, is calculated as:

$$VSWR = (1 + Vr/Vf)/(1 - Vr/Vf)$$
$$= (1 + SQRT(Pr/Pf))/(1 - SQRT(Pr/Pf))$$

where Vr and Vt represent the reflected and transmitted voltage, and Pr and Pt represent the reflected and transmitted power. Maximum power transfer to the transducer (efficiency=100%) corresponds to VSWR of 1. In the embodiment described herein, the circuit for driving each channel is tuned to minimize VSWR to at least 1.5 in order to achieve an efficiency of greater than 95%.

Extending the Number of Channels

The circuit layout associated with the illustrated control kernel 14 implements up to 64 independently controlled channels. If the number of channels increases beyond 64, the logic gates within the FPGA 24(1-N) may be insufficient to provide 8-bit phase resolution.

To extend the number of channels implemented by the control kernel 14, the MCU/FPGA modules 26(1-N) are operated in parallel and synchronized. All the MCU/FPGA modules 26(1-N) are connected to a single master MCU 20. This extends the system to as much as 64*N channels. Theoretically there is no limit to extending the number of MCU/FPGA modules 26(1-N).

Phased Array Selection

Figure 5:
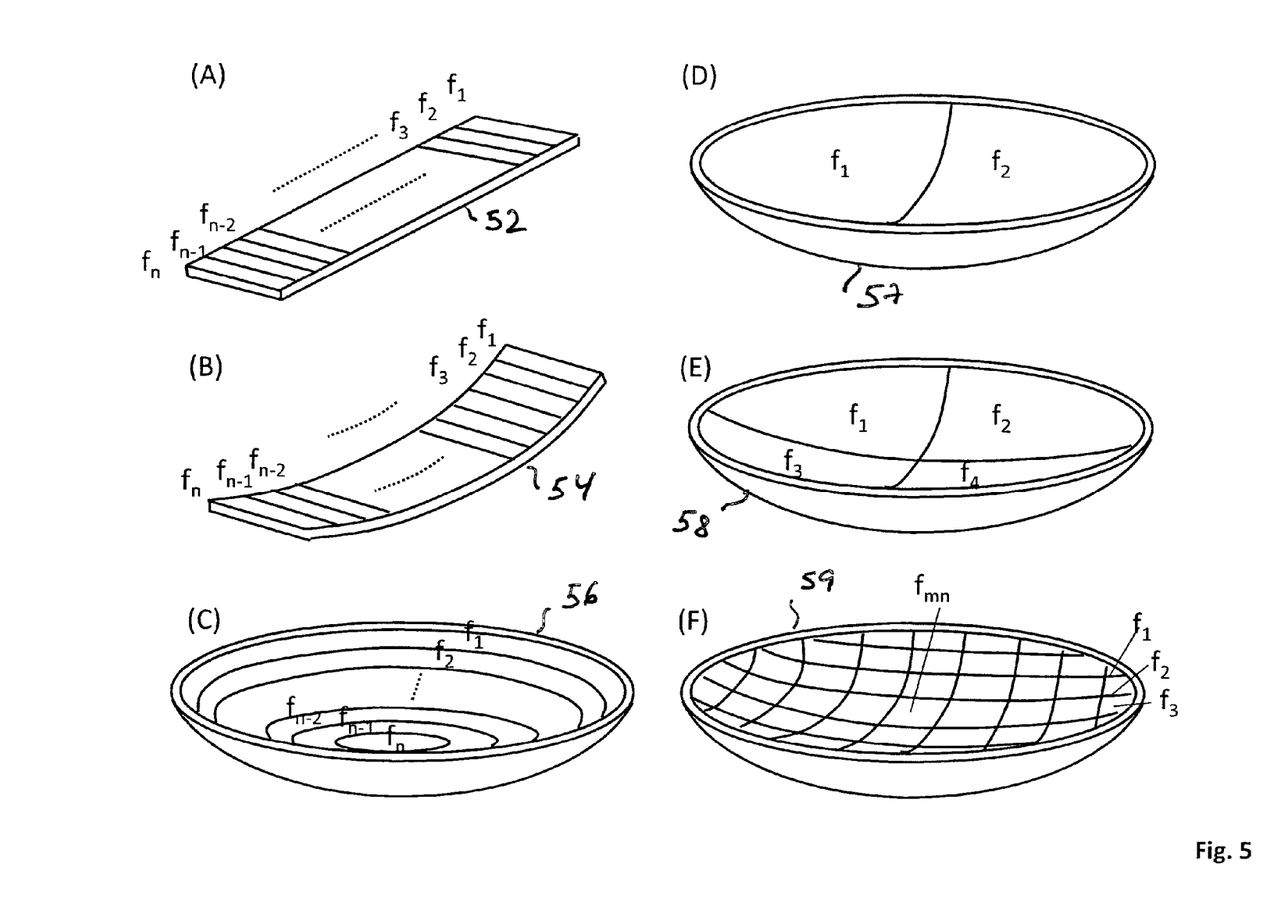
FIGS. 5A-5F show exemplary ultrasonic phased arrays provided as output loads for the driving system of FIG. 1.

The driving module 16 ultimately drives, as its load, either a one-dimensional or two dimensional phased array. FIGS. 5A and 5B show examples of one-dimensional phased arrays 52, 54 with one-dimensional dicing of the piezoelectric material along the elevation direction. Such an array can be a flat array 52, as shown in FIG. 5A, or a curved array 54, as shown in FIG. 5B.

A one-dimensional phased array 52, 54 diced into N independent elements, when coupled with a driving system having more than N independent driving channels, can be used to generate ultrasonic energy output. The phase and the frequency of each element can be designed and combined arbitrarily when the system contains M independent simultaneous frequency selections, where M is greater than N. If M is less than N, it is no longer possible to simultaneously produce N different frequency outputs. In that case, the element for purposes of driving would not correspond to a particular channel, but would instead correspond to a set of channels, or a "driving group."

A similar principle can be applied to other phased array configurations, such as curved arrays formed from an annularly diced transducer 56, shown in FIG. 5C, from a transducer 57 bifurcated along its diameter to form two elements, shown in FIG. 5D, a quarter-cut four element spherical curved transducer 58, shown in FIG. 5E, or a two-dimensional spherical curved transducer 59, shown in FIG. 5F.

Implementations

Figure 6:
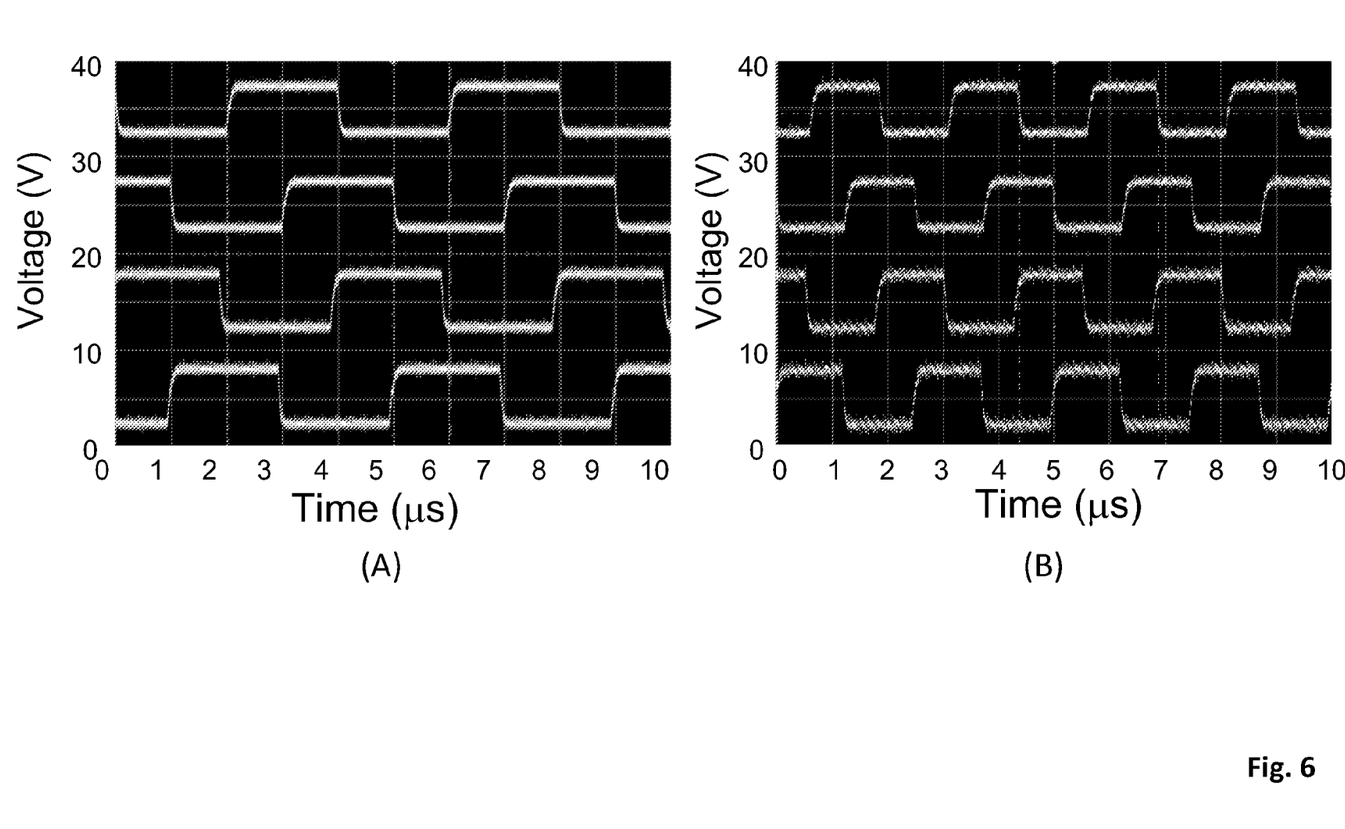
FIG. 6 shows four randomly assigned four channels operating with signal outputs having relative phases of 0, 90, 180, and 270 degrees at 250 kHz and at 400 kHz.
Figure 7:
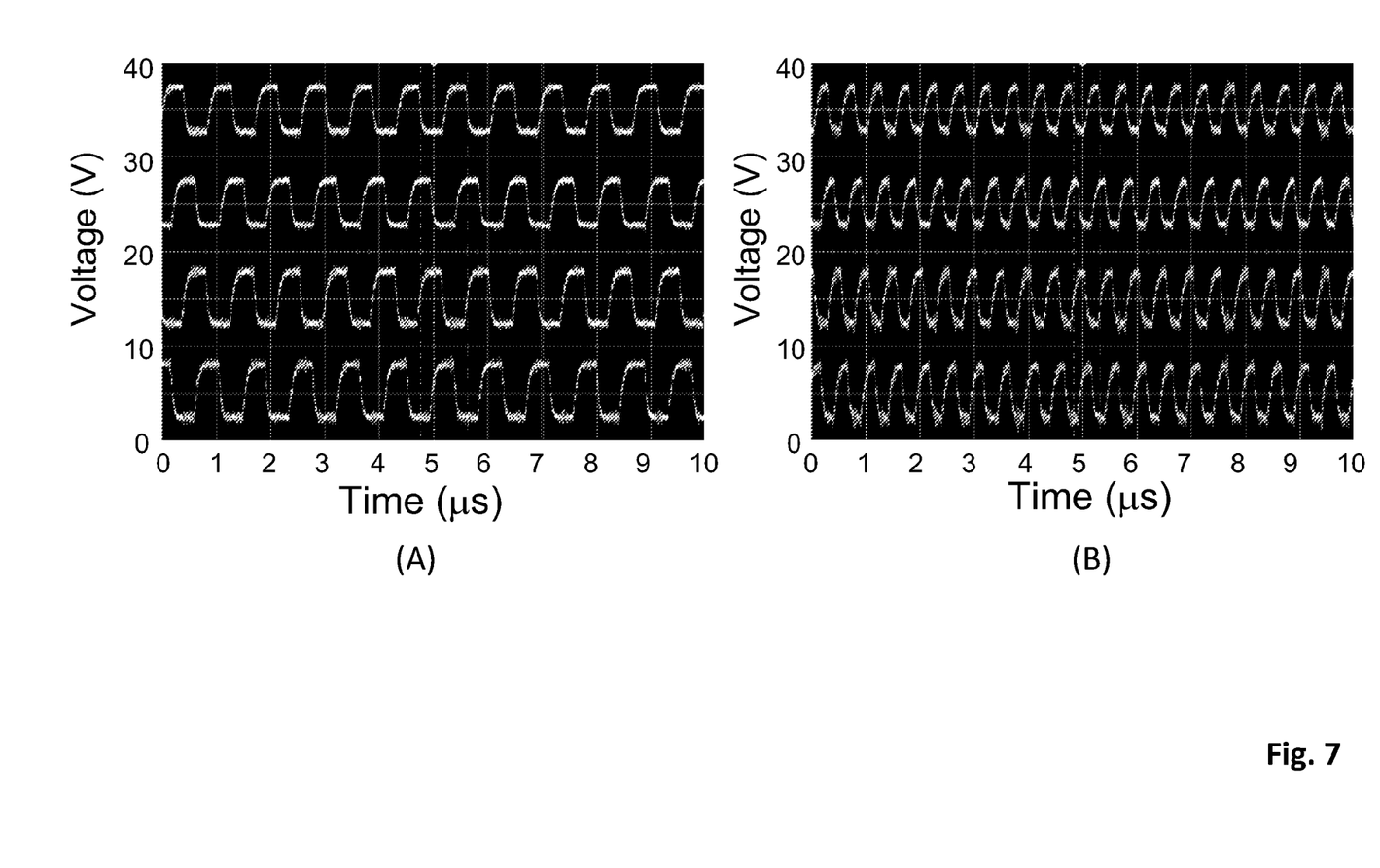
FIG. 7 shows four randomly assigned channels operating with signal outputs of 0, 90, 180, and 270 degrees at 1.2 MHz and at 2 MHz.

FIGS. 6 and 7 show outputs from an implementation that generates a multiple frequency RF signal output from the control kernel 14, and that operates with precise relative phase control. FIG. 6 shows that by randomly assigning four channels to operate at 250 kHz and four more to operate at 400 kHz, one can precisely output phasing signals with their relative phase controlled to be 0, 90, 180, and 270 degrees, respectively. Similarly, FIG. 7 shows that by randomly assigning four channels to operate at 1.2 MHz and 2 MHz, one can precisely output phasing signals with their relative phase controlled to be 0, 90, 180, and 270 degrees, respectively.

Figure 8:
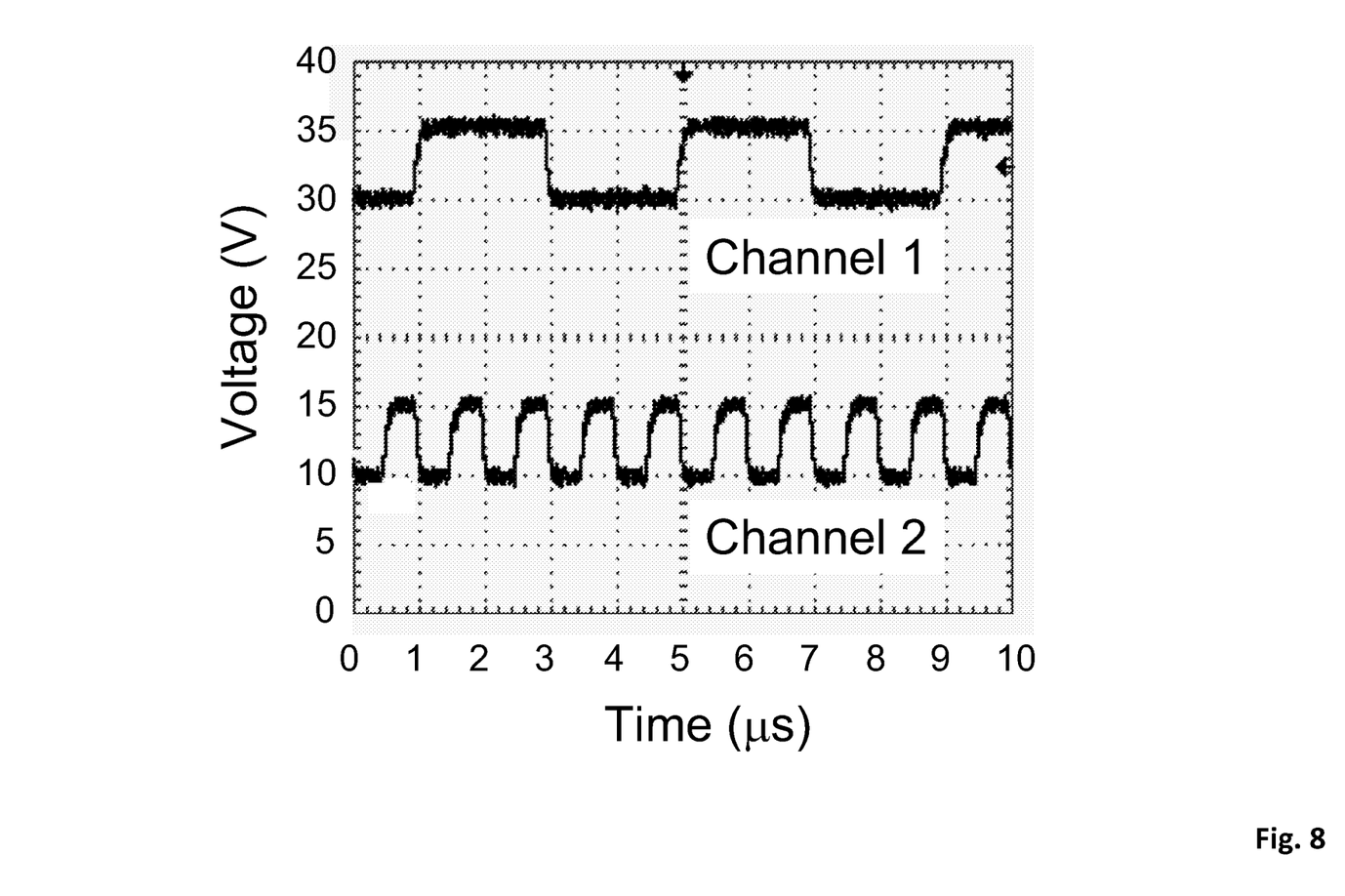
FIG. 8 shows two randomly assigned channels operating at 250 kHz and 1 MHz.

In addition to being able to produce phasing signals with a tunable driving frequency, the control kernel 14 can also produce more than one frequency at the same time. For example, FIG. 8 shows an output from two channels, one of which carries a 250 kHz signal and another carrying a 1 MHz signal. As is apparent, the architecture described herein can output multiple frequencies simultaneously from the driving module 16. As a result, the architecture described herein is capable of enhancing cavitation and/or thermal ablation.

Figure 9:
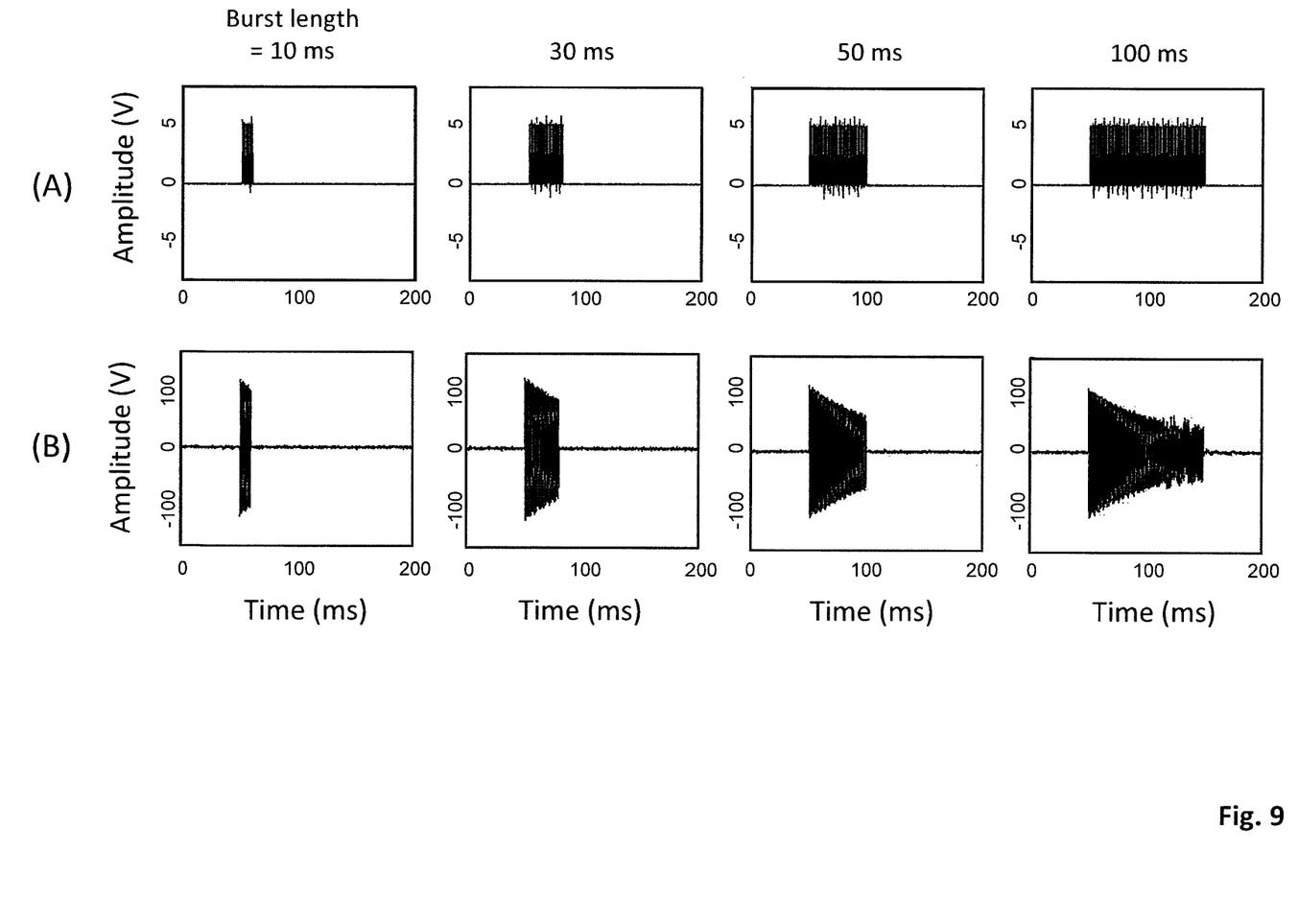
FIG. 9 shows a randomly assigned channel with output driving signals for operating at burst mode at four different burst lengths: 10 milliseconds, 30 milliseconds, 50 milliseconds, and 100 milliseconds, and with a pulse repetition frequency of 1 Hz, with the top row showing the driving signals measured at an output of a buffer shown in FIG. 1, and the bottom row showing amplified signals measured at an output of the driving module shown in FIG. 1.

The preceding figures show the control kernel 14 producing continuous wave (CW) output. However, the control kernel 14 can also produce burst mode output. As shown in FIG. 9, output signals can be controlled to have burst lengths ranging from 10 milliseconds to 100 milliseconds. Burst mode operation is particularly useful because the gap between bursts enables heat to dissipate, thus limiting thermal damage to adjacent tissue.

Figure 10:
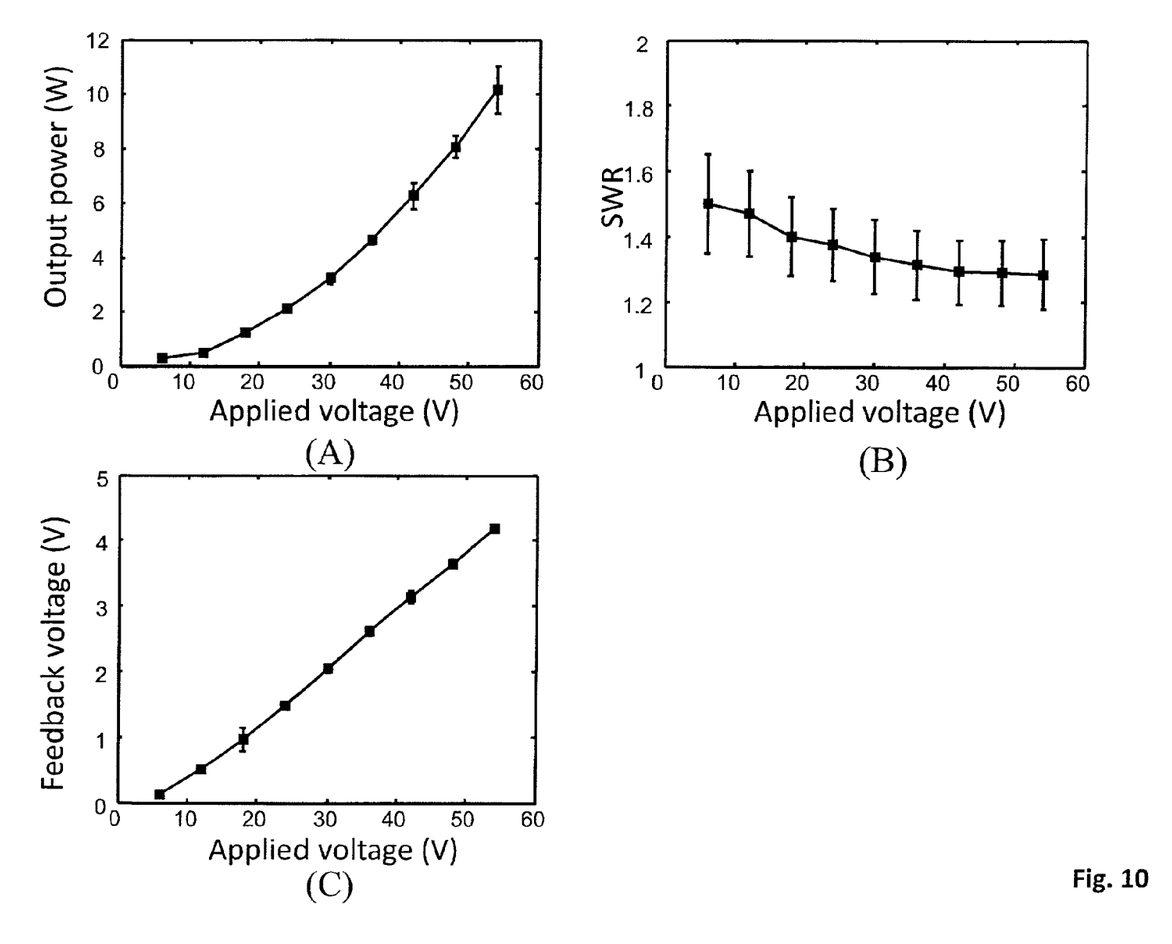
FIG. 10 shows mean and standard deviations of SWR and feedback voltage measurements.

FIGS. 10A-C illustrates the kernel's ability to regulate output power.

FIG. 10A shows the relationship between applied voltage and output power in a 31-channel array. As the applied voltage increased from 5 to 55 V, the output power increased linearly from 0.3 to about 10 W, with only small variations among the 31 channels. This effect was achieved by monitoring a pre-established voltage-to-power lookup table to regulate the output power.

FIG. 10B further shows the SWR as monitored using the directional coupler. The measured SWR was less than 1.5 in most cases for most applied voltages. This indicated a forward-transmit power efficiency of more than 95%. The SWR was slightly lower at small power outputs, but still reasonably close to 1.5.

FIG. 10C shows that the feedback voltage was close to being a linear function of the applied voltage. The high linearity between the output and feedback voltage arose from a linear voltage-to-voltage conversion circuit design. The minimal variations among the 31 channels suggested that variance arising from heterogeneous components was also minimal. As a result of this linear relationship, the output voltage could easily be detected by linearly scaling the feedback voltage, and the output power could be transformed from the output voltage by using an established look-up table. These two functions were be embedded in a FPGA memory and are easily upgradeable.

The driving apparatus described herein enables an operator to use a GUI for controlling frequency tunability and for causing generation of multiple frequencies. In addition, the apparatus achieves both power control with 8-bit resolution and phase control on a per channel basis with 8 bits of resolution, and the ability to monitor, in real time, the power transmitted to any channel and the power reflected back from that channel.

The ability to generate multiple frequencies is useful for standing wave suppression when sonicating a body cavity, such as the cranium or abdomen.

For thermal therapy, the apparatus described herein allows one to ablate a larger volume of tissue with each sonication by combining basebands (f) and harmonics (e.g., 2 f, 3 f . . . ), super-harmonics (e.g., 1.5 f, 2.5 f . . . ), and sub-harmonics (e.g., 0.5 f) thereof, or arbitrary frequencies, at the output of selected transducers.

With regard to cavitation enhancement, for example for improving gene transduction, drug delivery, sonophoresis, or other acoustic effects having clinical or biological applications, the apparatus described herein permits enhancement of such effects by combining a baseband frequency with harmonics, super-harmonics, and sub-harmonics as described above.

Finally, the ability to generate two output frequencies permits generation of a beat signal based on the difference between the two applied frequencies. Such a beat signal is useful for diagnostic purposes, such as detection of temperature changes, or radiation force mapping.

The invention claimed is:

1. An apparatus for sonicating a patient, said apparatus comprising:
an ultrasound array having a plurality of transducers;
a driving module for driving said transducers;
a control kernel configured to cause said driving module to drive said transducers concurrently at two different frequencies, wherein the control kernel comprises: a master microcontrol unit and a plurality of slave microcontrol units, each of said slave microcontrol units configured to control a subset of said transducers, wherein said master microcontrol unit provides instructions to said slave microcontrol units;
and a dual stage voltage controlled oscillator/phase locked loop (VCO/PLL) circuit comprising: a first stage that receives a waveform having a first particular frequency and scales that first particular frequency by a first scale factor, and a second stage that receives a waveform having a second particular frequency and scales that second particular frequency by a second scale factor.

2. The apparatus of claim 1, further comprising: a plurality of floating point gate arrays, and wherein each of the slave microcontrol units is in data communication with a subset of said gate arrays.

3. The apparatus of claim 1, further comprising a plurality of multiplexers, each of which receives waveforms having different frequencies, and wherein each of said slave microcontrollers is configured to select, from each of a subset of said multiplexers, a waveform having a particular frequency.

4. The apparatus of claim 1, further comprising a power sensing circuit for providing, to the control kernel, information concerning an extent to which power is output by said transducers.

5. The apparatus of claim 1, wherein said control kernel is further configured to drive at least one of said transducers at at least two frequencies simultaneously.

6. An apparatus for sonicating a patient, said apparatus comprising:
   an ultrasound array having a plurality of transducers;
   a driving module for driving said transducers;
   means for causing said driving module to drive said transducers concurrently at two different frequencies;
   and a dual stage voltage controlled oscillator/phase locked loop (VCO/PLL) circuit comprising: a first stage that receives a waveform having a first particular frequency and scales that first particular frequency by a first scale factor, and a second stage that receives a waveform having a second particular frequency and scales that second particular frequency by a second scale factor.

7. A method for sonicating a target, said method comprising:
   directing an ultrasound array having a plurality of transducers toward said target;
   selecting a plurality of frequencies;
   causing said array to concurrently illuminate said target using each of said frequencies by providing a master and a plurality of slave, each slave being configured to control a subset of transducers, said master being configured to provide instructions to a slave for causing said slave to control said transducers;
   and providing a dual stage voltage controlled oscillator/phase locked loop (VCO/PLL) circuit comprising: a first stage that receives a waveform having a first particular frequency and scaling that first particular frequency by a first scale factor, and a second stage that receives a waveform having a second particular frequency and scaling that second particular frequency by a second scale factor.

8. The method of claim 7, wherein causing said array to concurrently illuminate comprises causing different transducers to be excited at different frequencies.

9. The method of claim 7, wherein causing said array to concurrently illuminate comprises causing a transducer to be concurrently excited at different frequencies.

10. The method of claim 7, further comprising providing feedback indicative of an extent to which power is output by said array.

11. The method of claim 7, further comprising providing floating point gate arrays, and providing data communication between each slave and a subset of said gate arrays.

* * * * *